United States Patent [19]

Nishino

[11] 3,976,936

[45] Aug. 24, 1976

[54] NON-DESTRUCTIVE METAL INSPECTION APPARATUS USING A SHARP-POINTED PIN AND COIL FOR PRODUCING EDDY CURRENTS IN THE INSPECTED ARTICLE

[75] Inventor: Eizo Nishino, Kitakyushu, Japan

[73] Assignee: Nihon Densokki Kabushiki Kaisha, Kitakyushu, Japan

[22] Filed: Sept. 11, 1974

[21] Appl. No.: 505,202

[30] Foreign Application Priority Data

| | | |
|---|---|---|
| Feb. 23, 1974 | Japan | 49-21036 |
| Feb. 28, 1974 | Japan | 49-24072 |
| June 27, 1974 | Japan | 49-74911 |

[52] U.S. Cl. ................................................. 324/37
[51] Int. Cl.² .......................................... G02R 33/12
[58] Field of Search ................................ 324/37, 40

[56] References Cited
UNITED STATES PATENTS

| | | | |
|---|---|---|---|
| 2,353,211 | 7/1944 | Zuschlag | 324/40 |
| 3,271,664 | 9/1966 | Mountz et al. | 324/40 |
| 3,336,527 | 8/1967 | Paulson et al. | 324/40 |

FOREIGN PATENTS OR APPLICATIONS

| | | | |
|---|---|---|---|
| 624,719 | 8/1961 | Canada | 324/37 |
| 650,012 | 10/1962 | Canada | 324/37 |
| 661,496 | 4/1963 | Canada | 324/40 |
| 936,033 | 9/1963 | United Kingdom | 324/40 |
| 991,890 | 5/1965 | United Kingdom | 324/40 |

OTHER PUBLICATIONS

Nerwin, H.; Eddy Current Testing of Tubular Steel Products; Mat. Eval.; Apr. 1966; pp. 192–196.

*Primary Examiner*—Robert J. Corcoran
*Attorney, Agent, or Firm*—Haseltine, Lake & Waters

[57] ABSTRACT

An eddy current non-destructive metallic flaw inspection apparatus employing a pin coil detector. One end of the pin is made very sharp in order to effectively cause penetration of the concentrated magnetic flux emitted from the sharp point of the pin into the material to be inspected. An outside-type inspector is used to inspect rod products of ferromagnetic material. Two sets of pin coils radially confront to the product from its outside. An inside-type inspector is used to inspect pipe products. The inspector of this type is inserted within the pipe to be inspected and slides longitudinally along the pipe.

2 Claims, 9 Drawing Figures

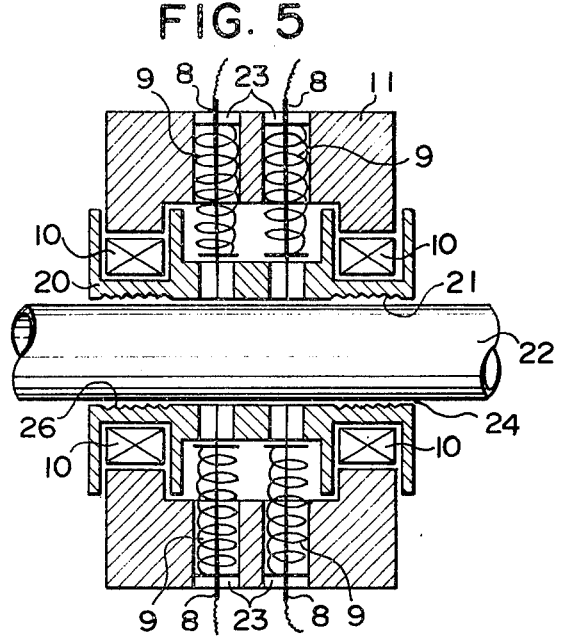
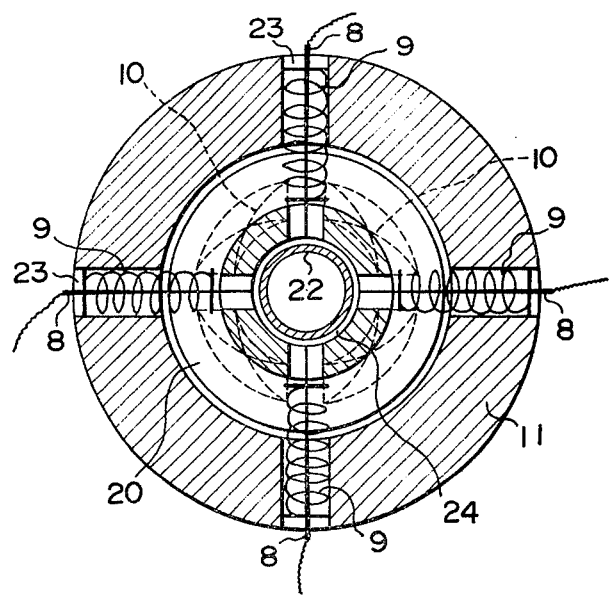

NON-DESTRUCTIVE METAL INSPECTION APPARATUS USING A SHARP-POINTED PIN AND COIL FOR PRODUCING EDDY CURRENTS IN THE INSPECTED ARTICLE

BACKGROUND OF THE INVENTION

1. Field of the Invention

The present invention relates to non-destructive metal inspection apparatus and more particularly to a pin coil-shaped detector adapted to be used in magnetized non-destructive type metal inspection apparatus.

2. Description of the Prior Art

Conventionally, various kinds of non-destructive type metal inspection methods and apparatus are known. These can be classified as the X-ray inspection method, ultrasonic flaw detecting method and a magnetic flaw detecting method. The magnetic flaw detecting method is divided into the magnetized powder inspection method using magnetized iron powder and the eddy current inspection method for inspecting a specimen to be tested by inducing an alternating current magnetic field in the specimen. The eddy current type metallic flaw inspection apparatus of the prior art requires a strong and large-size magnetizing apparatus so that it is laborious and uneconomical to produce the flaw inspection apparatus and perform the inspection. Further, the specimen to be inspected is limited to products made of nonmagnetic material. Moreover, the inspected specimen, stress-strain and magnetism diffusion along the surface are apt to be generated.

Therefore, if the eddy current type metallic flaw inspecting method and the apparatus therefor are applied to a ferromagnetic material, such as a steel plate or a steel tube, the material must be fully magnetized in order to inspect the products effectively and precisely.

That is to say, in order to cause an alternating magnetic field to penetrate into an inner portion of the ferromagnetic material to be inspected, it is necessary to fully magnetize a disturbed magnetic field in the material or effectively arrange the molecules in order in the material by passing a strong direct current magnetic field through the material to be inspected.

SUMMARY OF THE INVENTION

The present invention solves the above mentioned problems in the conventional techniques and provides an apparatus in which thin metal wire is wound around a pin, one end of which is sharp and alternating current is passed through this pin coil, whereby alternating magnetic lines of force emitted from the point at the end of the pin are focussed and penetrate deeply into the specimen to be inspected and eddy currents are developed in the depth of a specimen to be inspected so that effective inspection is obtained.

A first embodiment of the present invention is employed for a steel plate or the like composed of a ferromagnetic substance. In this embodiment, a detector provided with exciting coils disposed around the above mentioned pin coils is displaced along the surface of the specimen to be inspected whereby the inspecting operation is carried out. Said exciting coils may be substituted for the pin coils. In the first embodiment, pin coils are preferably used for exciting and inspecting purposes. It will be understood that during the inspecting operation the pointed end of the pin coil is directed towards a surface of the specimen to be inspected. Through the inspecting pin coil of this embodiment, alternating current flows and through the exciting coil direct current flows. Thus, owing to lines of magnetic force emitted from an end of the exciting coil, magnetic flux emitted from a central pin coil is effectively focussed without its diffusion along the surface of material to be tested. As above stated, said exciting coil may be advantageously used in a shape of pin.

The second embodiment of the present invention is adapted to be advantageously used for a member having a circular section such as a pipe or a rod member. In the second embodiment, pin coils are provided in a slider member and extend radially within the slider member which slides on the specimen to be inspected. Two sets of pin coils are placed in different positions in the longitudinal direction of the specimen to be inspected. This inspection apparatus having two sets of pin coils operates by carrying out a self-comparison method. Also in this embodiment, alternating lines of force emitted from the sharp end of the inspecting pin coil penetrates into the specimen to be inspected so that the eddy currents can be generated to a depth of material without surface diffusion of magnetism. According to the characteristics of this second embodiment, flaws of a pipe member are adapted to be inspected from inside thereof.

A third embodiment of the present invention is adapted to inspect a pipe member from the inside thereof. According to the embodiment, an effective inspections of cylindrical products are carried out by using an inspection apparatus having a plurality of pin coils extending at right angles to the wall of a projectile-shape carrier or slider which is displaceable in the pipe member. The third embodiment is the same as the second embodiment except for the exciting coil for exciting the pin coil inspector.

It will be apparent from the foregoing description that when the flaw inspecting apparatus according to the present invention is used, a high voltage source and a large-scale electric apparatus are not required and the degree of penetration of the flux emitted from these pin coils is large, so that even if the flaw detector is considerably spaced from the specimen to be inspected, the inspecting of flaws can be completely accomplished. Consequently, even if this specimen is heated to high temperature in order to rearrange the disturbed magnetic field inside the specimen or material to be inspected, the inspection apparatus is not subjected to damage due to high temperature and the operators will not be subjected to burns.

As apparent from the above description, the present invention provides a mechanism of much greater effectiveness than the conventional eddy current metallic flaw detector, and is particularly adapted to industrial fields.

OBJECTS OF THE INVENTION

A primary object of the present invention is to provide an eddy current type non-destructive metallic flaw inspection apparatus having a very simple structure and an excellent operational effect.

Another object of the present invention is to provide a non-destructive metallic inspection apparatus which is readily portable and adapted to function efficiently and effectively especially on an iron plate or a pipe of metal such as ferromagnetic material.

Still another object of the present invention is to provide a metallic flaw inspection apparatus adapted to cause a magnetic flux to be focussed deeply into an internal portion of a specimen to be inspected by using a pin around which a coil is wound.

Still another object of the present invention is to provide a very effective and convenient metallic flaw inspection apparatus adapted to inspect a pipe from outside by providing a pin coil in a carrier or slider displaceable longitudinally along the outer periphery of the pipe.

Still another object of the present invention is to provide a most effective flaw inspection apparatus adapted to inspect flaws in a pipe from inside thereof by providing a pin coil on a carrier or slider which is longitudinally displaceable inside the pipe.

Other objects and features will become apparent from the following description taken in conjunction with the accompanying drawings.

BRIEF DESCRIPTION OF THE DRAWING

FIG. 5 is a longitudinal sectional view of an outside-type flaw inspection apparatus for a pipe, FIG. 6 is a transverse cross sectional view of the inspection apparatus of FIG. 5 taken through a pin coil.

EXPLANATION OF PREFERRED EMBODIMENTS

Figure 1:
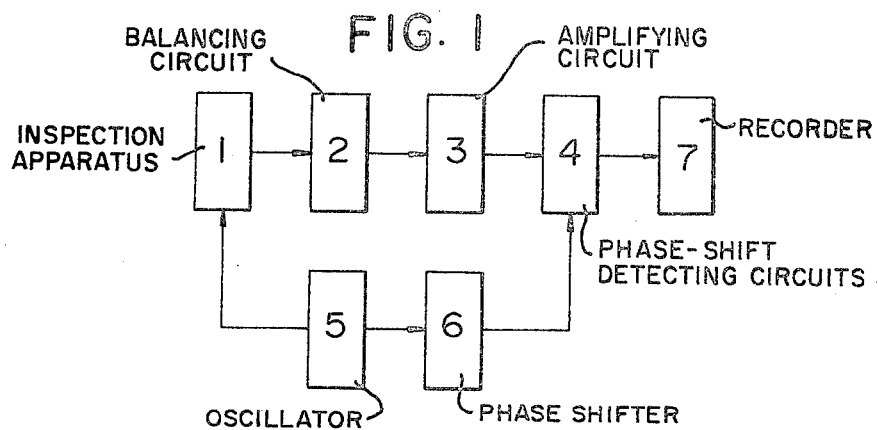
FIG. 1 is a block diagram of an inspection apparatus of the present invention.
Figure 2:
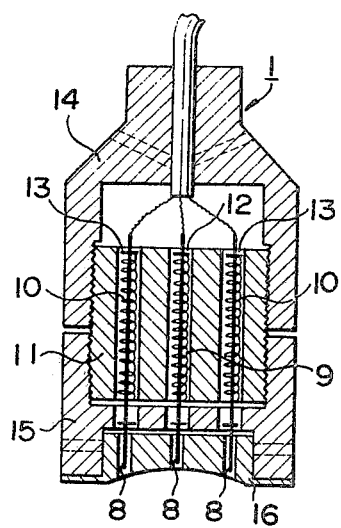
FIG. 2 is a sectional view of inspection apparatus used for an iron plate.
Figure 3:
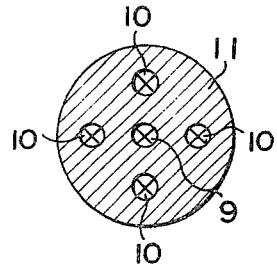
FIG. 3 is bottom view of the plane inspection apparatus of FIG. 2.

Referring to FIGS. 1 to 4 showing a first embodiment of the present invention, a pin coil type inspection apparatus 1, as shown in FIGS. 2 and 3, contains and supports a coil holder 11 by means of an upper case 14 and a lower case 15. At a center portion of the coil holder 11, a through-hole 12 is formed. At four locations around said through-hole 12, four additional through-holes 13 are formed. The through-holes are respectively equally spaced. In through-hole 12 an insepcting pin coil 9 is inserted and secured, and in throughholes 13 exciting pin coils 10 are secured respectively. Said inspecting pin coil 9 and said exciting pin coils 10 are formed by winding thin metallic wire around a thin core pin 8 an end of which is excessively sharp. The pin type core 8 is preferably ferromagnetic metal. Furthermore, the polarity of the exciting pin coils 10 is in the same direction. Reference numerals 16 designates a slider. This slider has a shape convenient for being mounted and slid on a specimen to be inspected. The pins of the inspecting pin coil 9 and the exciting poi pin coils 10 extend through the lower case 15 and into the slider 16 and the ends 8 of the pins comfront the lower end face of the slider. Through the inspecting pin coil 9, alternating current flows and through the exciting pin coils 10, direct current flows. FIG. 1 is a block diagram of the apparatus for inspecting metallic flaws. Reference numeral 2 of the block diagram shows a balancing circuit, 3 an amplifying circuit 4 a phaseshift detecting circuit, 5 an oscillator, 6 a phase shifter, and 7 a recorder.

Metallic flaw inspection according to the present invention will be described hereinbelow.

The inspecting pin coil 9 is connected to the oscillator 5 so as to generate an alternating magnetic field and connected to the balanced circuit 2. The exciting pin coils 10 are connected to a direct current power source (not shown). The inspection apparatus of the present invention is examined by the use of a pin coil electromagnetic oscillating apparatus or inspection apparatus 1 as a standard specimen and the balance of the balanced circuit 2 is maintained. Next, the pin coil electromagnetic oscillating apparatus or flaw detector 1 is placed to confront the slider on a ferromagnetic specimen to be inspected and is displaced thereon.

In consequence, the flux of the exciting pin coils 10 deeply penetrate into the specimen to be inspected and the portion where inspecting pin coil 9 confronts it is magnetized and the internal magnetic field of the ferromagnetic specimen to be inspected is arranged in order. In this case, the polarity of the exciting pin coils 10 are in the same direction, so that flux emitted from respective ends of the pins 8 is repeled from each other and focusingly advances towards and into the specimen to be inspected and the specimen effectively is magnetized in deep portion thereof. Next, alternating magnetic field generating in the inspecting pin coil 9 penetrates into the specimen to be inspected from the sharp end of the pin 8 of the inspecting pin coil 9 and reaches a deep portion of the specimen to be inspected and thereby eddy currents are generated not only in the surface of the specimen to be inspected but also in an inner portion thereof. The change of this eddy current is detected by means of inspecting pin coil 9 and its output is supplied to the input of the balancing circuit 2. The balance of said circuit 2 is made in advance by means of a standard specimen. When there are flaws or unevenness in thickness in the specimen to be inspected, the balanced condition of the balancing circuit 2 is broken and an output is obtained. This output is transmitted to the recorder 7 through the amplifying circuit 3, and the phase-shift detecting circuit 4. On said recorder 7 the output wave form is recorded so as to determine whether there are flaws or changes in thickness or not.

Figure 4:
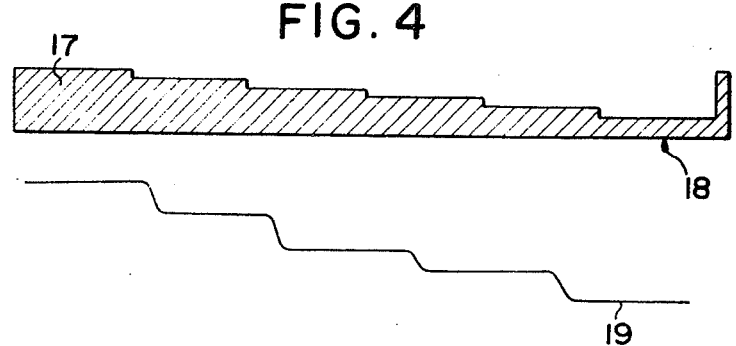
FIG. 4 shows a specimen to be inspected and an output curve of the inspection apparatus.

When a test piece of steel plate 17 is inspected by the use of the apparatus of the present invention, changes in thickness of a specimen 18 to be inspected can be determined or discriminated by viewing the output wave 19, as shown in FIG. 4.

The second embodiment of the present invention will be described with reference to FIGS. 5 and 6 and this embodiment comprises a substantially cylindrically shaped slider 20 having a through-hole 24 in a center portion through which a specimen 22 to be inspected is inserted and slided. Two exciting coils 10 are provided on both ends of the slider 20 on its outer periphery. The polarity of the exciting coils 10 are in the same direction. Reference numeral 21 is a screw thread formed, in a portion adjacent the exciting coil 10, on an inner circumferential surface of said slider. On the outer periphery of the slider 20, the cylindrical coil holder 11 is fitted and secured. Through-holes 23 are formed in the slider and open radially in the slider. These through-holes are located at four locations on the coil holder 11 and are directed towards a center portion thereof. Within said through-holes 23, pin coils 9 are inserted and secured. Each pin coil 9 is formed by winding a metallic wire around a thin pin 8 one end of which is sharp. Said pin 8 is preferably formed of ferromagnetic metal. An end of the pin of each pin coil 9 penetrates into the slider 20 and confronts the inner circumferential surface of the slider. Through said exciting coils 10, direct current flows and through each said pin coil 9, alternating current flows.

The operation of the second embodiment of the present invention will be explained hereinbelow. The exciting coil 10 is connected to a direct current power source (not shown). Each pair of pin coils 9, is connected to oscillator 5 and a balanced circuit 2. When a ferromagnetic specimen 22 to be inspected is inserted through through-hole 24 of slider 20, the specimen is effectively magnetized by means of exciting coils 10. An alternating magnetic field from each pin coil 9 is focussed into specimen 22 from the sharp end of pin 8, whereby eddy currents are generated in the specimen 22. When the specimen 22 is advanced along the through hole 24, the eddy currents generated in the specimen 22 by each pair of pin coils 9 are equalized and accordingly balance of the balanced circuit 2 is maintained. However, if there exist flaws or changes in thickness in the specimen to be inspected, a difference in the eddy current generated in the specimen by each pair of inspecting pin coils 9, is produced and then the balanced of the balanced circuit is broken, so that an output signal is obtained. Said output signal is transmitted to the recorder 7 through the amplifying circuit 3 and the phase-shift detecting circuit 4 and its wave form is recorded in order to reveal any defects in the specimen 22.

Figure 7:
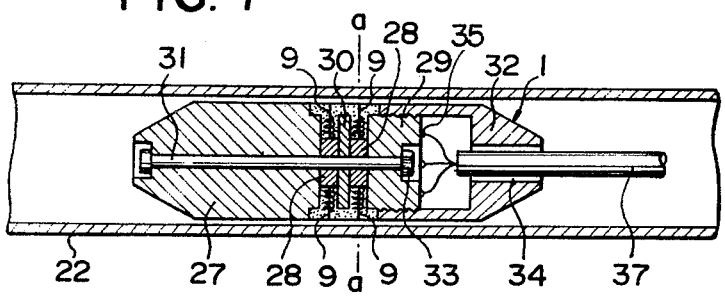
FIG. 7 is a longitudinal sectional view of an insidetype inspection apparatus for a pipe.
Figure 8:
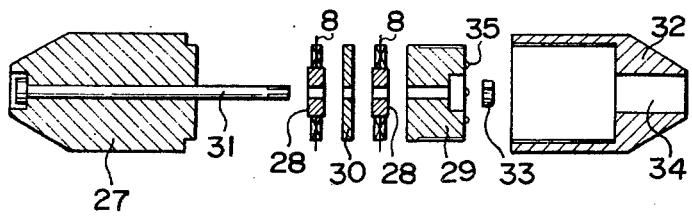
FIG. 8 is an exploded view of the inspection apparatus of FIG. 7
Figure 9:
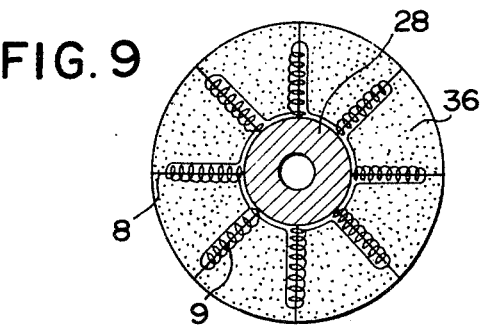
FIG. 9 is a cross sectional view through the inspection apparatus of FIG. 7 taken on line a-a through a pin coil.

The third embodiment of the present invention will be described in detail in conjunction with FIGS. 7, 8, and 9.

A fastening means 31 is inserted into a center portion of a substantially cylindrical head 27. Two coil seats or holders 28, and a threaded member 29 are fitted on said fastening means 31 in order. Between said two coil seats, a partition 30 is placed. Said threaded member 24 has a male thread portion at its outer periphery. These members are integrally fastened to each other by means of a nut 33. Said threaded member 29 is threadedly secured to a closure member 32 to assemble the inspection device. On the outer periphery of each said coil seat 28, a plurality of pin coils 9 are positioned so as to protrude radially therefrom, the spacing between the pin coils 9 being equal. Each pin coil 9 isformed by winding a thin conductor around a pin 8 one end of which is very sharp. The pin 8 is ideally a ferromagnetic metal.

Reference numeral 34 is a through-hole into which a lead wire 37 is inserted. Said lead wire is connected to a terminal 35 to which both ends of the conductor are connected. Numeral 36 is designates a holder made of a synthetic resin material which fills and is solidified on the outer periphery of the coil seats 28, so as to secure the pin coils 9. Numeral 22 shows a piper to be inspected.

The third embodiment of the present invention effects metallic flaw inspection as described hereinbelow. The inspection apparatus 1 is connected oscillator 5 and balanced circuit 2 by means of lead wire 37 and an alternating magnetic field is generated in each apparatus 9. When the inspection coil 1 is inserted into a pipe to be inspected, the flux of the alternating magnetic field generating in each pin coil 9 is focussed into an inner portion of the pipe 22. Eddy currents are caused to be generated not only on the surface of the pipe to be inspected but also in the inner portion thereof. When the inspection apparatus 1 is mechanically or manually displaced in the pipe 22, the eddy currents generated are in the pipe equalized when the pipe has no defects by means of each pair of pin coils embracing the partition wall 30 and consequently the balance of the balanced circuit 2 is kept. However, when there are flaws or changes in thickness in the pipe 22, a change in the eddy currents in the pipe 22 is generated, change in coil impedance of each pin coil 9 is produced and the balance of the balanced circuit is broken and thus an output signal is obtained. This output signal is transmitted to recorder 7 through the amplifying circuit 3 and the phase-shift detecting circuit 4 and it is represented as a wave form 19 in order to permit detection of flaws or defects in the inspected member, i.e., pin 22.

What is claimed is:

1. Eddy current flow inspection apparatus comprising an inspection core constituted by at least one thin core pin having a pointed end, a pluraitiy of exciting cores including respective thin pins with pointed ends circumferentially arranged around the core pin, a first conductor wound around the inspection core pin and adapted for being connected to a AC power source to induce eddy currents into the member to be inspected, a plurality of second conductors respectively wound around the exciting pins and adapted for being connected to a DC power source to magnetize the member to be inspected, a holder having through-holes therein in a number corresponding to that of said inspection and exciting core pins for holding said coils and cores within the holes to direct and confront said pointed ends at the member to be inspected with a slight clearance, and means connected to the first conductor to monitor changes in the eddy currents due to flaws.

2. Apparatus according to claim 1 further comprising a slider of generally plate-like shape adapted to be moved on the member to be inspected, said slider having through holes in which said pins extend, a housing to which the slider is secured, said holder being of cylindrical shape and disposed in said housing, said inspection coil and core extending longitudinally through a center one of said holes in the holder, said exciting coils and cores extending longitudinally in the remaining holes in said holder which are disposed at positions surrounding said inspection coil and core.

* * * * *